United States Patent
Rahman et al.

(10) Patent No.: US 7,399,888 B2
(45) Date of Patent: Jul. 15, 2008

(54) ANTICONVULSANT COMPOUNDS

(75) Inventors: Attaur Rahman, Karachi (PK); Mohammad Iqbal Choudhary, Karachi (PK); Farzana Shaheen, Karachi (PK); Arun Ganesan, Southampton (GB); Shabana Usman Simjee, Karachi (PK); A. Mohsin Raza, Karachi (PK)

(73) Assignee: HEJ Research Institute Karachi University, Karaschi (PK)

( * ) Notice: Subject to any disclaimer, the term of this patent is extended or adjusted under 35 U.S.C. 154(b) by 57 days.

(21) Appl. No.: 11/307,251

(22) Filed: Jul. 1, 2006

(65) Prior Publication Data

US 2008/0004353 A1     Jan. 3, 2008

(51) Int. Cl.
*C07C 49/21*     (2006.01)
*A61K 31/12*     (2006.01)
(52) U.S. Cl. .................. 568/377; 568/378; 514/690
(58) Field of Classification Search .................. None
See application file for complete search history.

(56) References Cited

U.S. PATENT DOCUMENTS 3,780,743 A * 12/1973 Roberts .................. 131/276

* cited by examiner

*Primary Examiner*—Sikarl A. Witherspoon
(74) *Attorney, Agent, or Firm*—Sarfaraz K. Niazi

(57) ABSTRACT

The invention relates to novel isoxylitones and their use as anticonvulsant and in the treatment of a variety of disorders.

1 Claim, 2 Drawing Sheets

Isoxylitone B (2-Propanone, 1-(3,5,5-trimethyl-2-cyclohexen-1-ylidene)-, (1Z)

Isoxylitone A
(2-Propanone, 1-(3,5,5-trimethyl-2-cyclohexen-1-ylidene) (1E)

ANTICONVULSANT COMPOUNDS

This invention relates to novel compounds, to processes for preparing them, and to their use as therapeutic agents.

This invention is based on investigations on a plant which has been anecdotally used as anticonvulsant but without recognizing the source of its activity or structure of the chemical thereof. *Delphinium* (Ranunculaceae) is a genus comprising annual or perennial erect, hardy ornamental herbs and about 270 species of *Delphinium* are found world wide [Reidl and Nasir in Flora of Pakistan, Ali, S. I. Nasir, Y. J. Eds.; National Herbarium, Pakistan Agricultural Research Council Islamabad, 1991 p. 41). *Delphinium denudatum* Wall is extensively found in the Western Himalayas and in Kashmir. The roots of this plant known as Jadwar have been used in traditional system of medicine for a number of purposes. The roots have been used in the Unani system of medicine for the treatment of epilepsy (Said, H. M., Hamdard Pharmacopoeia of Eastern Medicine; Hamdard National Foundation, Times Press, Karachi, 1970, p. 49). Bioassay-guided isolation studies on this plant were carried out to isolate anticonvulsant constituents of this plant. The crude ethanolic extract of this plant was subjected to bioassay-guided fractionation which revealed that chloroform extracts containing diterpenoid alkaloids were highly toxic to neuromuscular system of mice (Raza et. al., Abstract, Am. College of Toxicol., 1997, 123). It was found that anticonvulsant constituents were found in least toxic of all extracts, the non-alkaloidal aqueous extract of plant. The aqueous extract was further subjected to vacuum liquid chromatography which afforded oily fraction (FS-1) by elution with acetone [inhibition of sustained repetitive firing in cultured hippocampal neurons by an aqueous fraction isolated from *Delphinium denudatum*, M. Raza, F. Shaheen, M. I. Choudhary, S. Sombati, Atta-ur-Rahman and R. John. DeLorenzo, *J Ethnopharmacol.* 90 (23): 367-74 (2004); In vitro Inhibition of pentylenetetrazole and bicuculline induced epileptiform activity in rat hippocampal neurons by aqueous fraction isolated from *Delphinium denudatum*. M. Raza, F. Shaheen, S. Sombati, M. I. Choudhary, Atta-ur-Rahman and R. John. DeLorenzo, *Neuroscence Letters*, 333, 103-106 (2002); Anticonvulsant effect of FS-1 isolated from roots of *Delphinium denudatum* on hippocampal pyramidal neurons. M. Raza, F. Shaheen, M. I. Choudhary, Atta-ur-Rahman, S. Sombati, A. Suria and R. J. DeLorenzo, *Phytotherapy Research*, 17, 38-43 (2003); Anticonvulsant activities of ethanolic extract and aqueous fraction isolated from *Delphinium denudatum*. M. Raza, S. Sombati, F. Shaheen, A. Suria, M. I. Choudhary, Atta-ur-Rahman and R. J. DeLorenzo, *Journal of Ethnopharmacology* 78, 1, 73-78, (2001); Anticonvulsant activities of the FS-1 sub fraction isolated from roots of *Delphinium denudatum*. M. Raza, S. Sombati, F. Shaheen, A. Suria, M. I. Choudhary, Atta-ur-Rahman and R. J. DeLorenzo, *Phytotherapy Research*, 15, 426-430, (2001)].

Prior art document U.S. Pat. No. 5,725,859 to Omer discloses a method of treating a patient infected with DNA virus of the herpes family or DNA hepatitis B or hepatitis C viruses, or suffering from chronic allergic rhino-sino-bronchitis, by administering to the said patient a pharmaceutical composition comprising at least two of the compounds selected from the group consisting of absinthe (*artemisia absinthium*) resin of mastic (resin *pistacia lenticus*) fruit of *delphinium denudatum* and wherein one or more of the compounds selected from the group consisting of rose buds (*flores rosae*) seeds of cardamom (*fructus ellettaria cardamomum*, and borage flowers (*flores onosma brateatum boriginaceae*) are added.

It has now been surprisingly found that isoxylitone compounds of formula IE and IZ (FIG. 1) representing the two isomers possess anticonvulsant activity and are therefore believed to be useful in the treatment and/or prevention of anxiety, mania, depression, panic disorders and/or aggression, disorders associated with a subarachnoid hemorrhage or neural shock, the effects associated withdrawal from substances of abuse such as cocaine, nicotine, alcohol and benzodiazepines, disorders treatable and/or preventable with anti-convulsive agents, such as epilepsy including posttraumatic epilepsy, Parkinson's disease, psychosis, migraine, cerebral ischemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia and narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS).

BRIEF DESCRIPTION OF DRAWING

FIG. 1 Structure of Isoxylitone A and B

Figure 1:
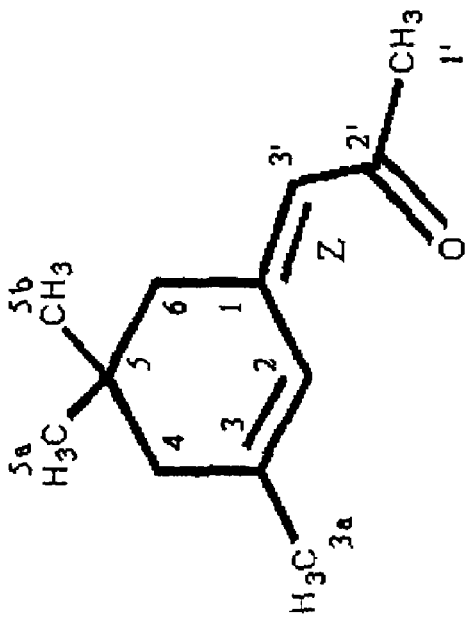
FIG. 1 is the chemical structure of the two isomers, isoxylitone A and isoxylitone B
Figure 1:
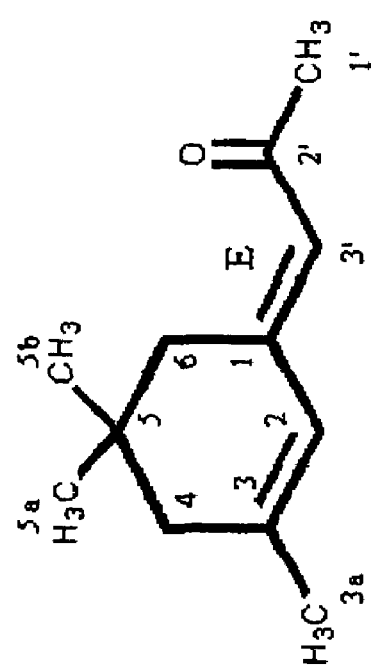
Figure 2:
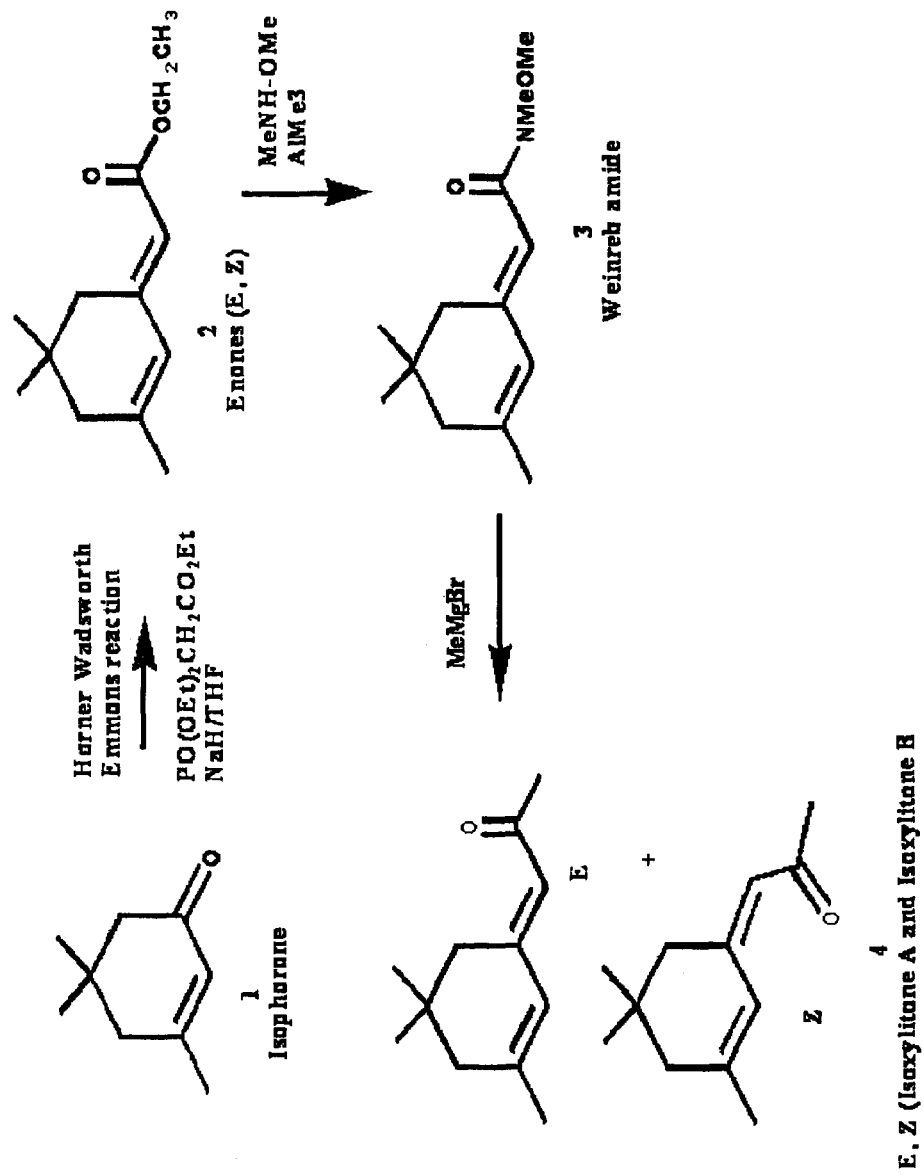
FIG. 2 is the Isolation of isoxylitone A and B from FS-1

The compounds and their salts may be obtained as solvates such as hydrates, and these also form part of this invention. The above compounds and pharmaceutically acceptable salts thereof, especially the hydrochloride, and pharmaceutically acceptable solvates, especially hydrates, form a preferred aspect of the present invention. The invention may contain either compound IE or IZ (FIG. 1) or a mixture thereof.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula IE or IZ (FIG. 1) are administered in the form of a unit dose composition, such as an oral unit dose including sub-lingual, rectal, topical or parenteral (especially intravenous) composition.

Such compositions are prepared by a mixture and are suitably adapted for oral or parenteral administration, and as such may be in the form of tablets, capsules, oral liquid preparations, powders, granules, lozenges, reconstitutable powders, injectable and infusible solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminum stearate gel or hydrogenated edible fats, emulsifying agents, for example lecithin, sorbitan monooleate, or acacia; nonaqueous vehicles (which may include edible oils), for example, almond oil, fractionated coconut oil, oily esters such as esters of glycerin, propylene glycol, or ethyl alcohol; preservatives, for example methyl or propyl p-hydroxybenzoate or sorbic acid, and if desired conventional flavoring or coloring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid hemorrhage or neural shock, the effects associated withdrawal from substances of abuse such as cocaine, nicotine, alcohol and benzodiazepines, disorders treatable and/or preventable with anticonvulsive agents, such as epilepsy including post-traumatic epilepsy, Parkinson's disease, psychosis, migraine, cerebral ischemia, Alzheimer's disease and other degenerative diseases such as Huntingdon's chorea) schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS) which comprises a compound of formula (IE and IZ, FIG. 1), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid hemorrhage or neural shock, the effects associated withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS) comprising administering to the sufferer in need thereof an effective or prophylactic amount of a compound of formula IE or IZ) or a pharmaceutically acceptable salt or solvate thereof.

In a further aspect the invention provides the use of a compound of formula IE or IZ, or a pharmaceutically acceptable salt or solvate thereof, for the manufacture of a medicament for the treatment and/or prophylaxis of anxiety, mania, depression, panic disorders and/or aggression, disorders associated with a subarachnoid hemorrhage or neural shock, the effects associated withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS).

In a further aspect the invention provides the use of a compound of formula IE or IZ, or a pharmaceutically acceptable salt or solvate, thereof as a therapeutic agent, in particular for the treatment and/or prophylaxis of anxiety, mania, depression , panic disorders and/or aggression, disorders associated with a subarachnoid haemorrhage or neural shock, the effects associated withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS).

Isolation of Isoxylitone A and B from FS-1

Dried roots were extracted in ethanol (1.4 kg) that yielded $LD_{50}$ of 774.5 mg/Kg and weak activity in MES (sc), PTZ and subcutaneous BIC tests; the aqueous extract (0.45 Kg) had stronger pharmacologic activity; this aqueous extract was evaporated under vacuum and further purification of aqueous extract yielded an oily fraction (FS-1) that showed strong pharmacologic activity, a column chromatography yielded The oily fraction Fs-1 was subjected to column chromatography on silica gel using isocratic solvent system (petroleum ether: chloroform, 8:2) as eluant which afforded several subfractions on the basis of TLC monitoring (petroleum ether: ethyl acetate, 9.9:0.1) and the solvent was removed in vacuum. The subtractions FSS (15-19 (1.9 Kg) that was subjected to preparative thin layer chromatography to yield isoxylitone A as 69.00 mg and isoxylitone B as 36.3 mg as two major compounds by using pet ether: ethyl acetate (9.9: 0.1) as developing solvent.

Isoxylitone A $R_f$=0.38 (Pet ether EtOAc, 9.9:0.1), $^1$H-, $^{13}$C-NMR δ (see Table-1), CIMS: m/z 179[M+1]+EIMS m/z (178, 163, 145, 135, 130, 105).

Isoxylitone B $R_f$=0.45 (Pet ether: EtOAc, 99:0.1), $^1$H-, $^{13}$-C-NMR δ (see Table-1). CIMS: m/z 179[M+1]+EIMS m/z (178, 163, 145, 135, 130, 105).

TABLE 1

$^1$HNMR AND $^{13}$CNMR Data of Isoxylitone A(E) and Isoxylitone B(Z)($d_6$-acetone δ ppm).

| C. No | Isoxylitone A(E) $^{13}$C(δ) | Isoxylitone A(E) $^1$H NMR, δ(J Hz) | Isoxylitone B(Z) $^{13}$C(δ) | Isoxylitone B(Z) $^1$H NMR, δ(J Hz) |
|---|---|---|---|---|
| 1 | 152.6(C) | — | 151.1(C) | — |
| 2 | 122.9(CH) | 6.02(bs) | 121.3(CH) | 7.38 |
| 3 | 147.5(C) | — | 148.3(C) | — |
| 3a | 24.3($CH_3$) | 1.82(bs) | 24.7($CH_3$) | 1.82(bs) |
| 4 | 39.5($CH_2$) | 1.97(m) | 46.2($CH_2$) | 1.99(m) |
| 5 | 31.8(C) | — | 32.1(C) | — |
| 5a | 28.5($CH_3$) | 0.90 | 28.3($CH_3$) | 0.90 |
| 5b | 28.5($CH_3$) | 0.90 | 28.3($CH_3$) | 0.90 |
| 6 | 45.4($CH_2$) | 2.70(d, J=1.8Hz) | 46.1($CH_2$) | 2.06(d, J=1.5Hz) |
| 1' | 31.8($CH_3$) | 2.09(s) | 31.8($CH_3$) | 2.09(s) |
| 2' | 198.3(C) | — | 197.7(C) | — |
| 3' | 125.5(CH) | 5.94 | 120.7(CH) | 5.82 |

Synthesis of Isoxylitone A (2-Propanone 1-(3,5,5-trimethyl-2-cyclohexen-1-ylidene) (1E) and Isoxylitone B (2-Propanone, 1-(3,5,5-trimethyl-2-cyclohexen-1-ylidene)-, (1Z).

The synthesis of isoxylitone A and B was started by using commercially available compound isophorone. The compound isophorone was treated with phosphonate ester (Horner Wadsworth Emmons reaction) to give esters 2 (E and Z). (N-Bensel, J. Hohn, H. Marschall and P. Weyerstahl, *Chem. Ber.* 112, 2256-2277). The resulted esters (2) were treated with N,O-dimethyl hydroxyl amine hydrochloride which afforded Weinreb amide (3) (step 2). The compound 3 was treated with Grignard reagent (MeMgBr) which afforded desired compounds Isoxylitone A(E) and Isoxylitone B(Z) (see scheme below).

Scheme of synthesis of Isoxylitone A and Isoxylitone B

Step 1: Reaction of Isophorone with Triethylphosphonoacetate:

Triethylphosphonate (50 mmol, 9.91 mL) was added dropwise to a slurry of 60% NaH (50 mmol, 2 g) in 100 mL of Dry THF. After addition the reaction mixture was stirred for 1 hour. Then isophrone (50 mmol 7.5 mL) was added to reaction mixture and refluxed for 20 hours. The progress of reaction was monitored through TLC. After the reflux of 20 hours reaction mixture was dissolved in water and extracted with ether and the ether extract was concentrated in vacuo, and purified by column chromatography by using solvent system, EtOAc,Hexane (1:9) which afforded desired enones in 79% yield. The product 2 were characterized on the basis of EIMS and $^1$HNMR data.

Step 2: Reaction of esters (2) with N,O-Dimethyl hydroxylamine hydrochloride: N,O-Dimethyl hydroxylamine hydrochloride (4.2 g) was taken in dry Dichloromethane (66 mL) under argon. The trimethyl aluminium Al $Me_3$ in 2 M hexane (43.26 nmol 4.2 g, 21.6 mL) was added dropwise under argon. The reaction mixture was stirred for 30 minutes. The mixture of esters (E+Z) were taken in 30 mL of dry dichloromethane and added to mixture. And refluxed for 28 hours during this time the reactant was completely consumed. The excess of Al $Me_3$ was quenched by adding 0.5 M HCl (60 mL) under argon at 0° C. The reaction mixture was neutralized by $NaHCO_3$ saturated solution. The organic layer was washed with brine and dried over anhydrous $Na_2SO_4$. The crude organic extract was purified by column chromatography [dichloromethane:methanol (9:1)] to yield Weinreb amide in 69% yield.

Step 3: Reaction of Weinreb Amide 3 with Grignard Reagent: Weinreb amide was taken in dry THF and stirred under argon at −780° C. Then MeMgBr in 3M ether was added and the reaction mixture was stirred at room temperature. When the reaction went to completion as checked by TLC, the reaction mixture was quenched by saturated solution of $NH_4Cl$ and aqueous layer was extracted with dichloromethane which afforded the crude extract which was purified by column chromatography to yield target compound isoxylitones A and B (E/Z isomers) in 90% yield.

After synthesizing these compounds they were tested in vivo model of epilepsy

Pharmacological testing of Isoxylitone A(E) and Isoxylitone B(Z)

Male NMRI albino mice weighing 19-22 g were housed in an environmentally regulated room on a 12 h light: 12 h dark cycle with 25±1° C. and had free access to food and water. The use of animals in experimental protocol was approved by the research committee of the ICCS, University of Karachi, in accordance with the international guidelines for the care and use of laboratory animals.

The anticonvulsant activity of compounds in mixture form was determined after intraperitoneal administration to NMRI mice weighing 19-22 g. Maximal electroshock (MES) and subcutaneous pentylenetetrazole (scPTZ) induced seizure models were used to test the anticonvulsant properties of compounds.

The E and Z mixture of compounds (1:2) at a dose of 10 mg/kg decreased the convulsive rate significantly in the MES model and blocked the hind limb tonic extension (HLTE)

elicited by electroshock in this test. Protection against HLTE in MEST predicts the ability of a testing material to prevent the spread of seizures discharge from the epileptic focus in brain in additions effectiveness in MEST correlates with efficacy in suppressing the generalized tonic-clonic and partial seizures. The tested compounds also showed anticonvulsant activity against scPTZ induced convulsions and significantly protected animals against PTZ induced HLTE or generalized body twitches. Anticonvulsant activity in the scPTZ test identifies compounds that can raise seizure threshold in the brain. These results were comparable to the reference antiepileptic drugs (AEDs) phenyloin and diazepam.

The results obtained in this study show that isoxylitone A and B have anticonvulsant activity and able to prevent convulsions in both the electrically and chemically-induced seizure models. Our results support additional studies to evaluate full therapeutic potential of this compound.

What is claimed is:

1. A method for the treatment of epilepsy or seizures comprising administration of an effective amount of 2-propanone-1,3,5,5-trimethyl-2-cyclohexen-1-ylidine or its isomers, salts or solvates, in a suitable pharmaceutical carrier, to humans and animals in need thereof.

* * * * *